US00PP13917P29

(12) United States Plant Patent

Bergman

(10) Patent No.: US PP13,917 P2

(45) Date of Patent: Jul. 1, 2003

(54) CHRYSANTHEMUM PLANT NAMED 'YOLAPORTE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,270

(22) Filed: Mar. 8, 2002

(51) Int. Cl.[7] ..... A01H 5/00

(52) U.S. Cl. ..... Plt./286

(58) Field of Search ..... Plt./286, 297, 298

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Yolaporte', characterized by its uniform and upright plant habit; strong and freely branching growth habit; dense dark green foliage; uniform and early flowering habit; large daisy-type inflorescences; spoon-shaped ray florets with dark purple-colored throats and light purple-colored tubes; and excellent postproduction longevity with plants maintaining good substance and color for about five weeks in an interior environment.

2 Drawing Sheets

BOTANICAL CLASSIFICATION/CULTIVAR DESIGNATION

*Chrysanthemum×morifolium* cultivar Yolaporte.

BACKGROUND OF THE INVENTION

The present Invention relates to a new and distinct cultivar of Chrysanthemum plant, botanically known as *Chrysanthemum×morifolium* and hereinafter referred to by the name 'Yolaporte'.

The new Chrysanthemum is a product of a planned breeding program conducted by the Inventor in Salinas, Calif. and Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in May, 1998, in Salinas, Calif., of a proprietary Chrysanthemum seedling selection identified as code number YB-4383, not patented, as the female, or seed, parent with a proprietary Chrysanthemum seedling selection identified as code number YB-5897, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and ray floret colors, fast response time, and excellent postproduction longevity.

Asexual reproduction of the new Chrysanthemum by vegetative tip cuttings was first conducted in Fort Myers, Fla. in June, 1999. Asexual reproduction by cuttings has shown that the unique features of this new Chrysanthemum are stable and reproduced true to type in successive generations.

SUMMARY OF THE INVENTION

The cultivar Yolaporte has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yolaporte'. These characteristics in combination distinguish 'Yolaporte' as a new and distinct Chrysanthemum:

1. Uniform and upright plant habit.
2. Strong and freely branching growth habit.
3. Dense dark green foliage.
4. Uniform flowering habit.
5. Early flowering, eight-week response time.
6. Large daisy-type inflorescences.
7. Spoon-shaped ray florets with dark purple-colored throats and light purple-colored tubes.
8. Excellent postproduction longevity with plants maintaining good substance and color for about five weeks in an interior environment.

Plants of the new Chrysanthemum differ primarily from plants of the female parent selection in ray floret shape and coloration as plants of the new Chrysanthemum have spoon-shaped ray florets with dark purple-colored throats whereas plants of the female parent selection have red purple-colored ray florets with short corolla tubes.

Plants of the new Chrysanthemum are shorter and have ray florets with darker purple-colored throats than plants of the male parent selection. In addition, inflorescences of plants of the new Chrysanthemum do not produce pollen whereas inflorescences of plants of the male parent selection produce pollen.

Plants of the new Chrysanthemum can be compared to plants of the cultivar Yoduluth, disclosed in U.S. Plant Pat. No. 11,993. In side-by-side comparisons conducted by the Inventor in Salinas, Calif., plants of the new Chrysanthemum differed from plants of the cultivar Yoduluth in the following characteristics:

1. Plants of the new Chrysanthemum were shorter and less vigorous than plants of the cultivar Yoduluth.

2. Plants of the new Chrysanthemum flowered more uniformly than plants of the cultivar Yoduluth.

3. Plants of the new Chrysanthemum flowered about one week earlier than plants of the cultivar Yoduluth.

4. Plants of the new Chrysanthemum had larger inflorescences than plants of the cultivar Yoduluth.

Plants of the new Chrysanthemum can also be compared to plants of the cultivar Rapture, disclosed in U.S. Plant Pat. No. 8,179. In side-by-side comparisons conducted by the Inventor in Salinas, Calif., plants of the new Chrysanthemum differed from plants of the cultivar Rapture in the following characteristics:

1. Plants of the new Chrysanthemum were more freely flowering but had smaller inflorescences than plants of the cultivar Rapture.

2. Ray florets of plants of the new Chrysanthemum had darker purple-colored throats than ray florets of plants of the cultivar Rapture.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the first sheet comprises a side perspective view of a typical flowering plant of 'Yolaporte' grown as a spray-type.

The photograph at the bottom of the first sheet comprises a close-up view of typical inflorescences of 'Yolaporte' grown as a spray-type.

The photograph at the top of the second sheet comprises a side perspective view of a typical flowering plant of 'Yolaporte' grown as a disbud-type.

The photograph at the bottom of the second sheet comprises a close-up view of typical inflorescences of 'Yolaporte' grown as a disbud-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as disbud and as spray-types. Measurements and numerical values represent averages of typical flowering plants.

Botanical classification: *Chrysanthemum×morifolium* cultivar Yolaporte.

Commercial classification: Daisy-type potted Chrysanthemum.

Parentage:

*Female, or seed, parent.*—Proprietary *Chrysanthemum×morifolium* seedling selection identified as code number YB-4383, not patented.

*Male, or pollen, parent.*—Proprietary *Chrysanthemum×morifolium* seedling selection identified as code number YB-5897,not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous daisy-type potted Chrysanthemum that can be grown as a disbud or as a spray-type. Stems mostly upright and somewhat outwardly spreading; uniform crown. Freely branching, about four lateral branches develop after removal of terminal apex (pinching); dense and full plants.

*Plant height.*—About 30 cm.

*Plant width.*—About 38 cm.

*Lateral branches (peduncles).*—Length: About 23.5 cm. Diameter: About 4 mm. Internode length: About 1.8 cm. Strength: Strong. Texture: Pubescent. Color: 146A.

*Foliage description.*—Arrangement: Alternate. Length: About 7.7 cm. Width: About 5.9 cm. Apex: Cuspidate to mucronate. Base: Truncate to attenuate. Margin: Palmately lobed, sinuses between lateral lobes mostly divergent. Texture: Upper surface: Sparsely pubescent. Lower surface: Pubescent; veins prominent. Color: Young foliage, upper surface: Darker than 147A. Young foliage, lower surface: Darker than 147B. Fully expanded foliage, upper surface: Darker than 147A. Fully expanded foliage, lower surface: 147B. Venation, upper surface: Close to 147A to 147B. Venation, lower surface: Close to 146A. Petiole length: About 2.9 cm. Petiole diameter: About 3 mm. Petiole color, both surfaces: Close to 146A to 146B.

Inflorescence description:

*Appearance.*—Daisy-type inflorescence form with elongated spoon-shaped ray florets. Inflorescences borne on terminals above foliage. Disk and ray florets arranged acropetally on a capitulum. Not fragrant. Can be grown as a disbud and as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for at about five weeks in an interior environment.

*Quantity of inflorescences.*—Grown as a disbud-type, only one inflorescence, the terminal inflorescence, develops per lateral branch. Grown as a spray-type, about 3 or 4 inflorescences develop per lateral branch.

*Inflorescence bud.*—Height: About 8 mm. Diameter: About 9 mm. Shape: Oblate. Color: Between 146A and 147A.

*Inflorescence size, plants grown as disbud-types.*—Diameter: About 11.2 cm. Depth (height): About 1.8 cm. Diameter of disc: About 2.5 cm. Receptacle diameter: About 1 cm.

*Inflorescence size, plants grown as spray-types.*—Diameter: About 9.8 cm. Depth (height): About 1.7 cm. Diameter of disc: About 2.1 cm. Receptacle diameter: About 8.5 mm.

*Ray florets.*—Shape: Spoon-shaped. Orientation: Initially upright, then about 80° from vertical. Aspect: Mostly straight. Size, plants grown as disbud-types: Length: About 5 cm. Corolla tube length: About 3.8 cm. Width: Open spoon: About 9 mm. Tube: About 5 mm. Size, plants grown as spray-types: Length: About 4.7 cm. Corolla tube length: About 4 cm. Width: Open spoon: About 8.5 mm. Tube: About 4.5 mm. Apex: Emarginate. Base: Fused into a corolla tube. Margin: Entire. Texture: Smooth, glabrous, satiny. Number of ray florets per inflorescence: About 32 arranged in a single row. Color: When opening and fully expanded, throat: Closest 71A. When opening and fully expanded, tube: Close to 155D underlain with 71A; overall tonality, close to 75A.

*Disc florets.*—Arrangement: Massed at center of receptacle. Shape: Tubular, elongated. Apex: Five-pointed. Size, plants grown as disbud-types: Length: About 6 mm. Width: Apex: About 2.25 mm. Base: About 2 mm. Size, plants grown as spray-types: Length: About 6 mm. Width: Apex: About 2.25 mm. Base: About 2.75 mm. Number of disc florets per inflorescence: Plants grown as disbud-types: About 210. Plants grown as spray-types: About 137. Color: Immature: Close to 154A. Mature: Apex: Close to 12A. Mid-section and base: Close to 146C.

*Phyllaries.*—Quantity per inflorescence: About 32. Length: About 8 mm. Width: About 3 mm. Shape: Ligulate. Apex: Acute. Base: Truncate. Texture: Upper surface: Waxy, smooth. Lower surface: Pubescent. Color, upper and lower surfaces: Between 146A and 147A.

*Peduncles, plants grown as spray-types.*—Length: First peduncle: About 4.5 cm. Fourth peduncle: About 5.5 cm. Diameter: About 2 mm. Angle to vertical: About 45 to 50° from vertical. Strength: Strong, flexible. Texture: Pubescent. Color: 146A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 12A.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yolaporte', as illustrated and described.

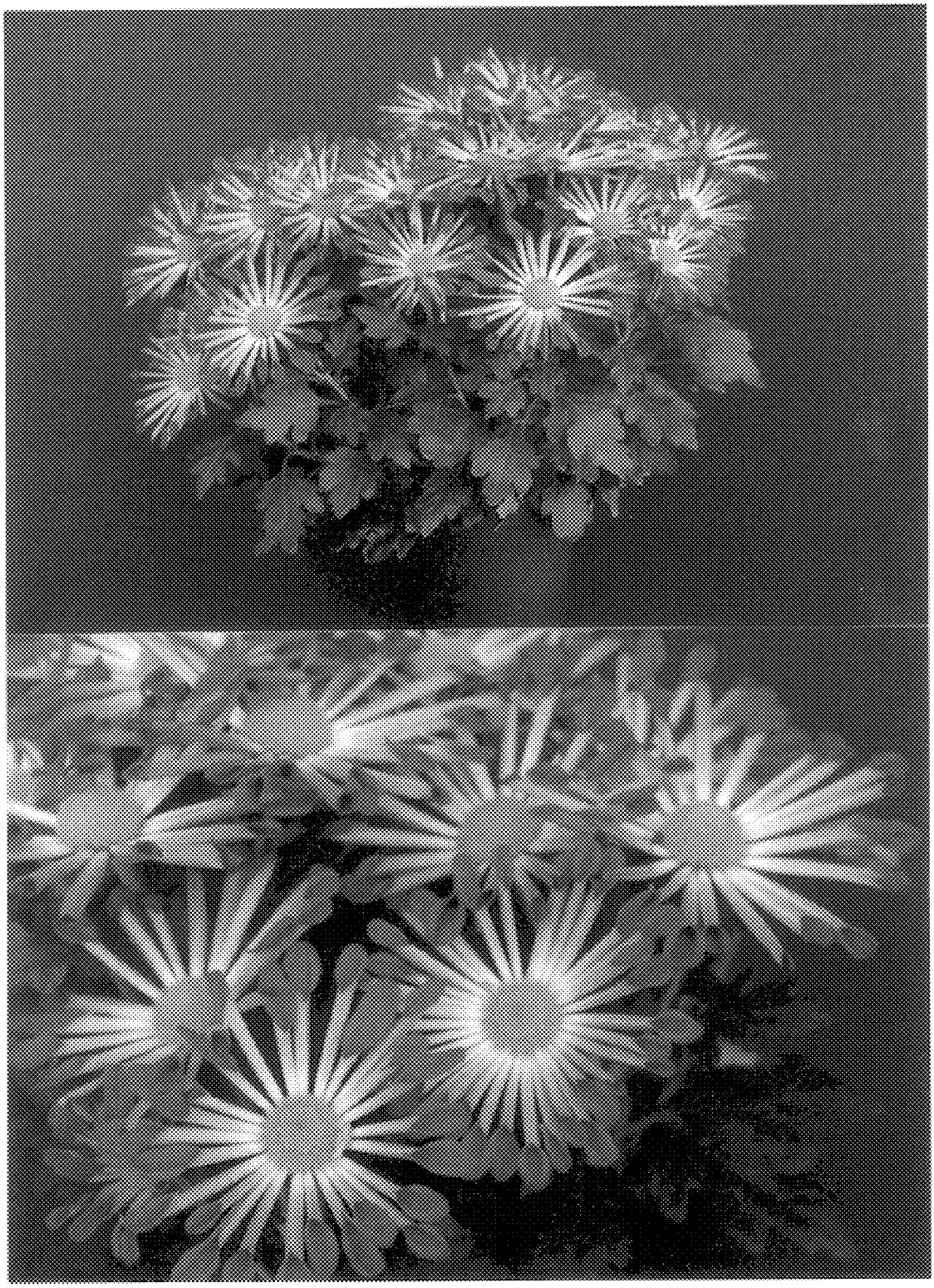

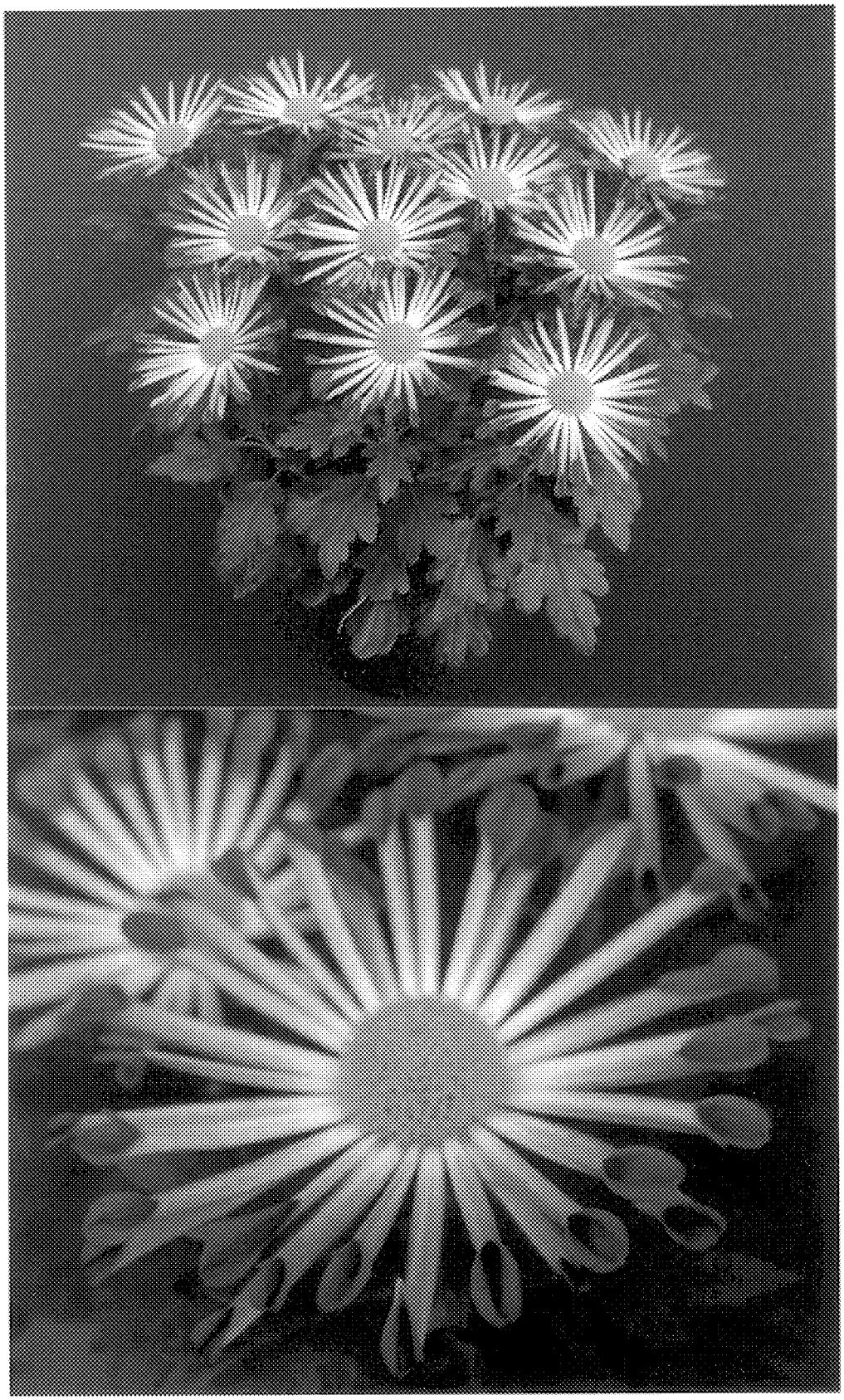

* * * * *